(12) United States Patent
Yazaki et al.

(10) Patent No.: US 7,790,451 B2
(45) Date of Patent: Sep. 7, 2010

(54) HSV WITH A MUSASHI PROMOTER REGULATING γ34.5 AND RIBONUCLEOTIDE REDUCTASE EXPRESSION

(75) Inventors: Takahito Yazaki, Tokyo (JP); Ryuichi Kanai, Tokyo (JP); Takeshi Kawase, Tokyo (JP); Hideyuki Okano, Tokyo (JP)

(73) Assignee: Keio University, Tokyo (JP)

( * ) Notice: Subject to any disclaimer, the term of this patent is extended or adjusted under 35 U.S.C. 154(b) by 118 days.

(21) Appl. No.: 12/091,633

(22) PCT Filed: Sep. 14, 2006

(86) PCT No.: PCT/JP2006/318304

§ 371 (c)(1),
(2), (4) Date: Apr. 25, 2008

(87) PCT Pub. No.: WO2007/049409

PCT Pub. Date: May 3, 2007

(65) Prior Publication Data

US 2009/0117644 A1   May 7, 2009

(30) Foreign Application Priority Data

Oct. 28, 2005 (JP) ............................. 2005-315414

(51) Int. Cl.
*C12N 15/00* (2006.01)
(52) U.S. Cl. .................................................. 435/320.1
(58) Field of Classification Search .................. 435/455, 435/320.1
See application file for complete search history.

(56) References Cited

FOREIGN PATENT DOCUMENTS

JP   2005-73653   3/2005

OTHER PUBLICATIONS

Chung et al. B-myb Promoter Retargeting of Herpes Simplex Virus Gamma 34.5 Gene-Mediated Virulence toward Tumor and Cycling Cells. J. Virol., 1999, vol. 73, pp. 7556-7564.*
Keyoung et al. High-Yield Selection and Extraction of Two Promoter-Defined Phenotypes of Neural Stem Cells from the Fetal Brain. NatureBiotechnology, 2001, vol. 19, pp. 843-850.*
Toda et al. Expression of the Neural RNA-Binding Protein Musashi1 in Human Gliomas. GLIA, 2001, vol. 34, pp. 1-7.*
Liu et al. ICP34.5 Deleted Herpes Simplex Virus with Enhanced Oncolytic, Immune Stimulating and Anit-Tumour Properties. Gene Therapy, 2003, vol. 10, pp. 292-303.*
Takahito Yazaki et al., "Atarashii Idenshi Kumikae Herpesvirus no Kaihatsu to Shinkei Koshu ni Taisuru Chiryo Koka," Dai 64 Kai Japan Neurosurgical Society Sokai, CD Rom Shorokushu, p. T0814-0-4, Sep. 22, 2005.

* cited by examiner

*Primary Examiner*—Deborah Crouch
(74) *Attorney, Agent, or Firm*—Kenneth H. Sonnenfeld; King & Spalding LLP

(57) ABSTRACT

The present invention provides a recombinant HSV having the ability to specifically kill tumor cells such as human glioma cells in vivo, useful and safe for treating human glioma, etc. and that can easily put to clinical use. A new recombinant HSV, KeM345, is constructed by inserting a γ34.5 gene transcription unit, which is expressed by Musashi1 promoter, into a ribonucleotide reductase gene site of the genome of a herpes simplex virus (HSV) previously attenuated, by means of homologous recombination and obtained as a purified strain. Since KeM345 is a recombinant virus itself, it can not only induce viral proliferation by being transmitted to culture cells but can also induce viral replication equivalent to that of wild-type HSV, showing an excellent cytotoxic effect (cytolytic ability) selectively upon a malignant glioma.

4 Claims, 10 Drawing Sheets

[Fig.1]
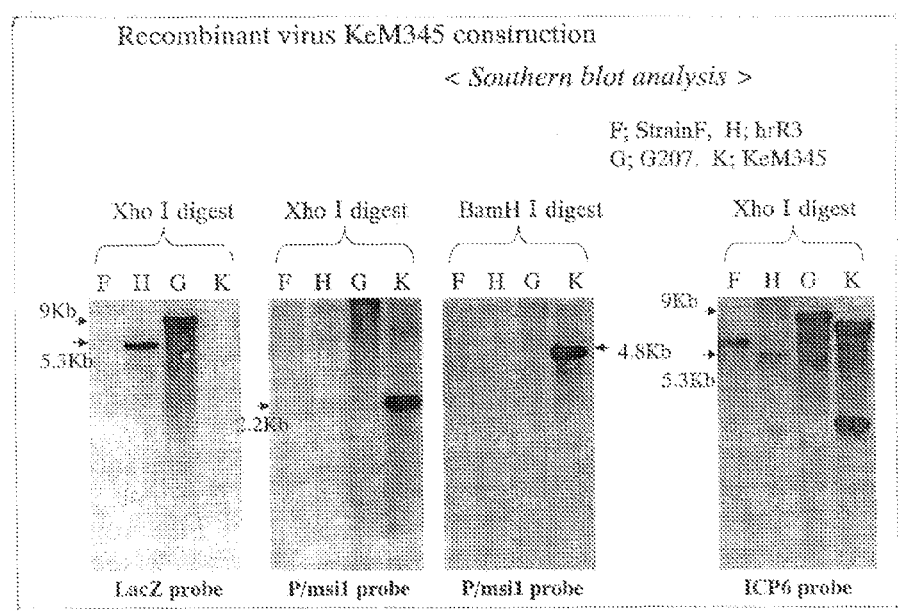
[Fig.2]
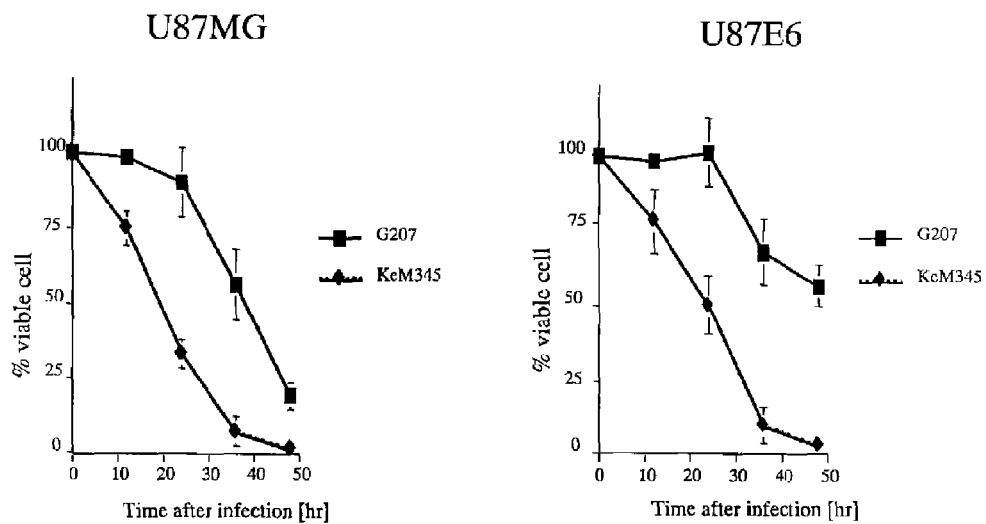

[Fig.3]
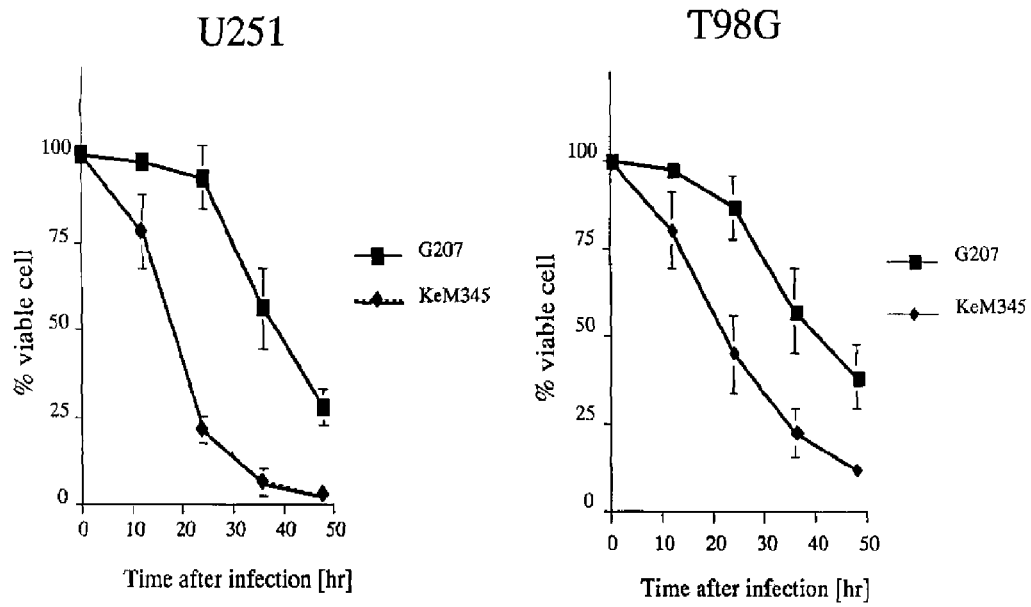
[Fig.4]
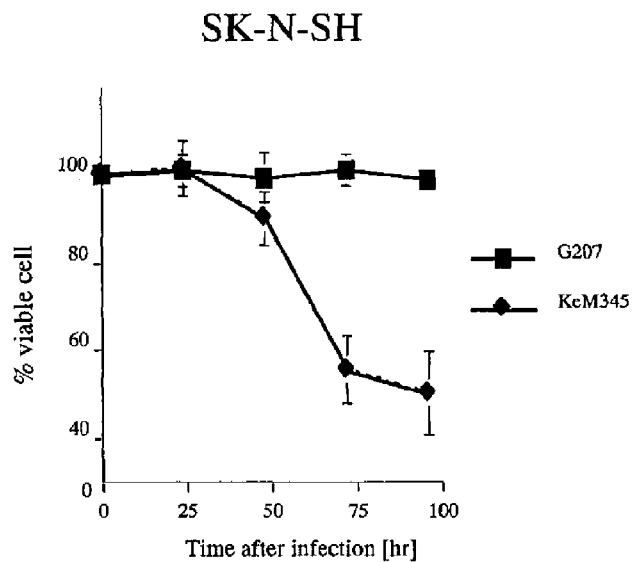

[Fig.5]
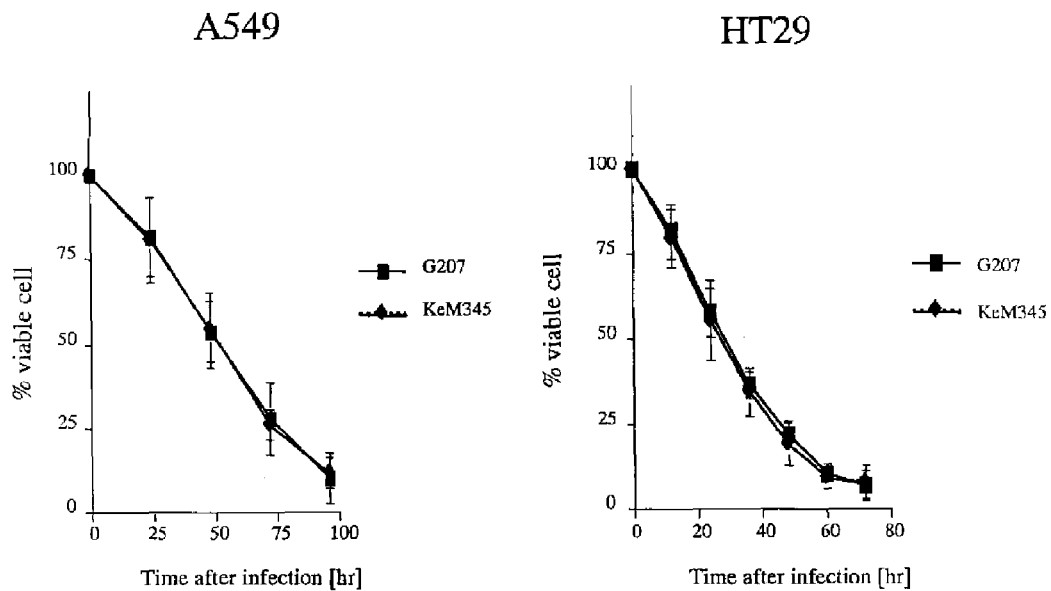
[Fig.6]
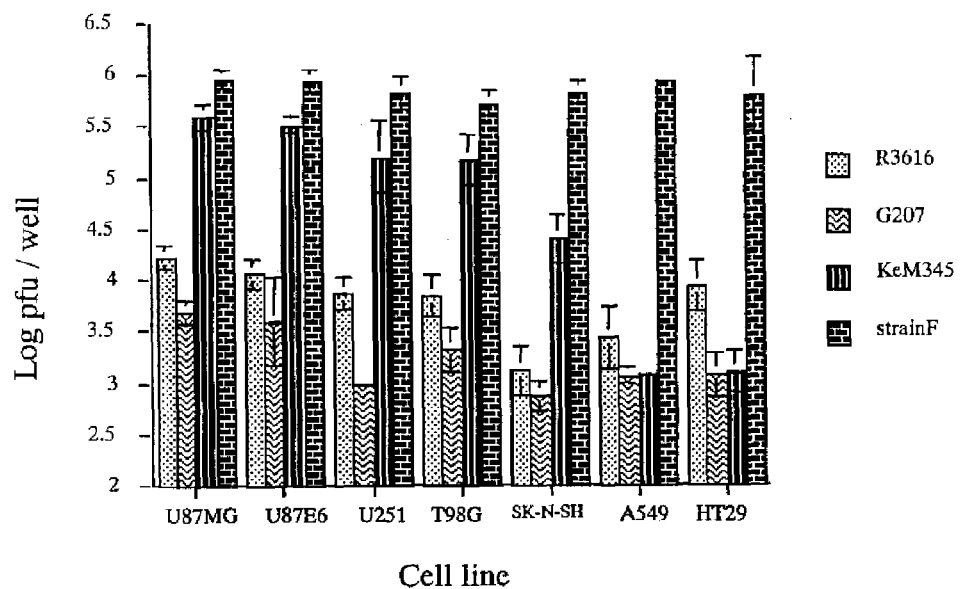

[Fig.7]
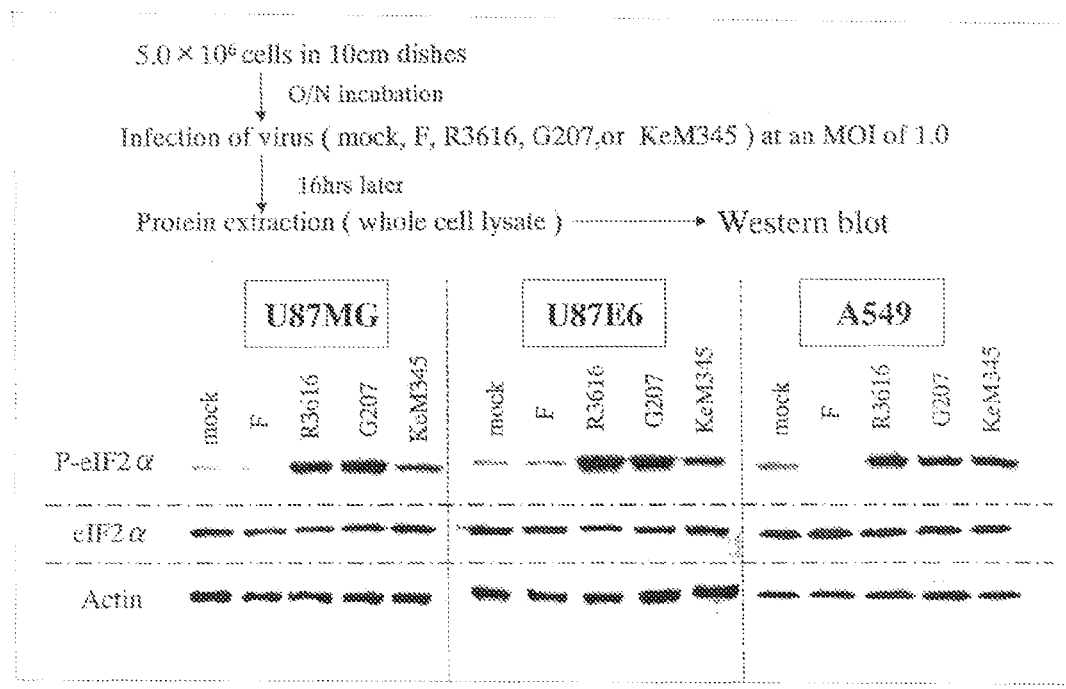
[Fig.8]
s. c. tumor model (U87E6)
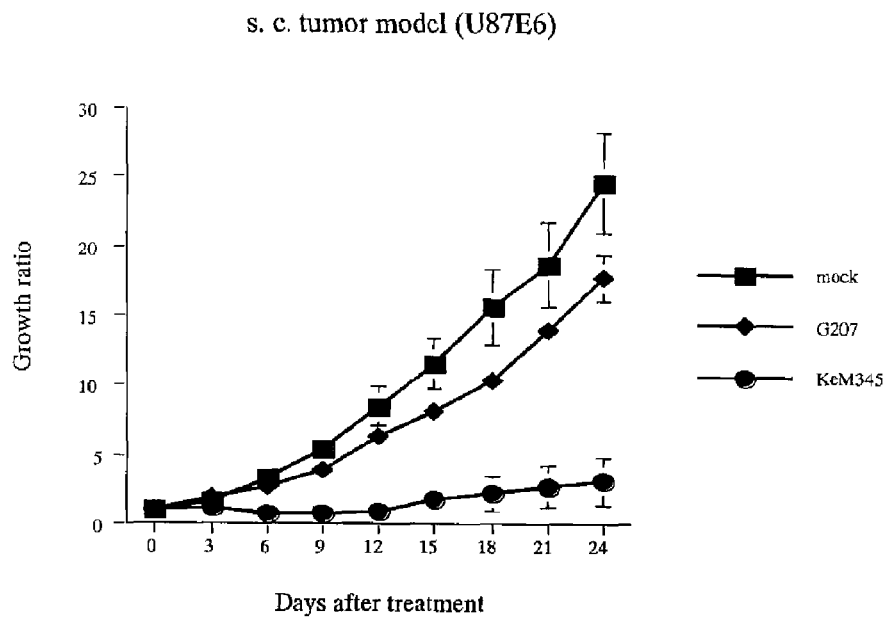

[Fig.9]
U87E6 intracerebral (xenograftic) tumor model
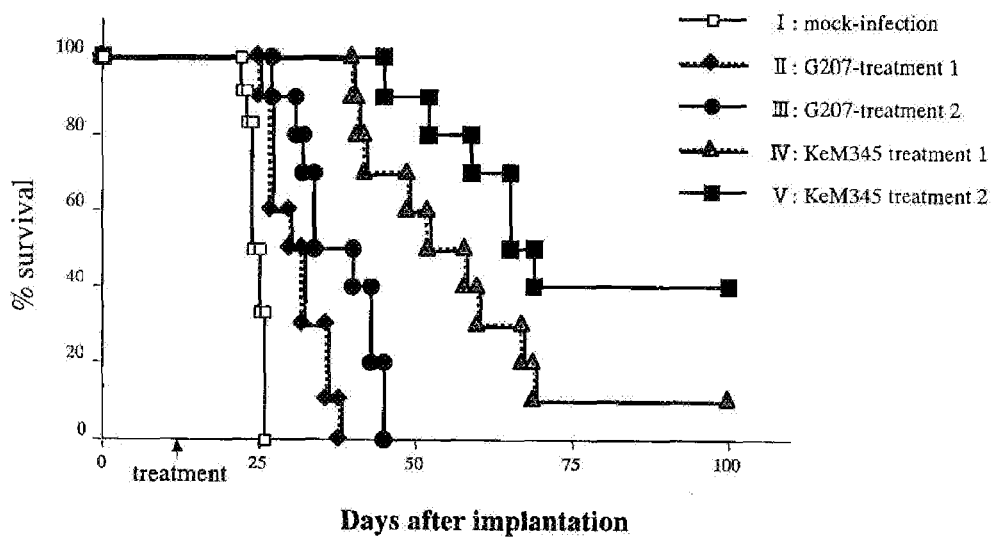
[Fig.10]
Intracerebral tumor model
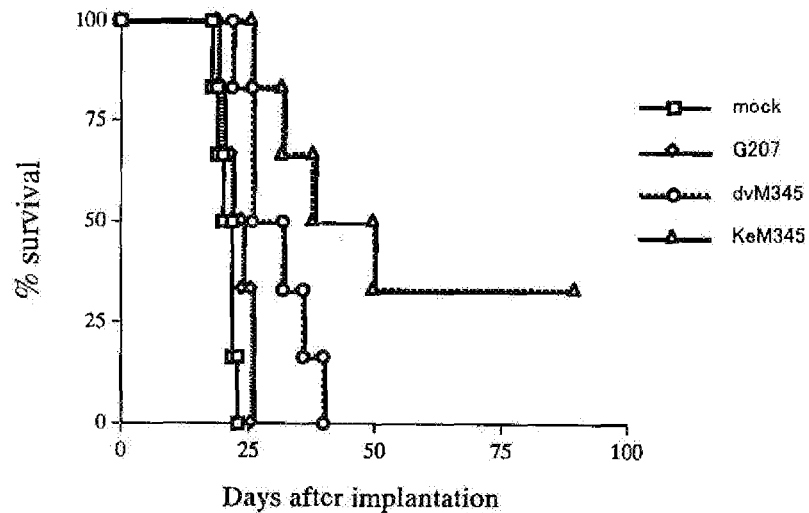

[Fig.11]
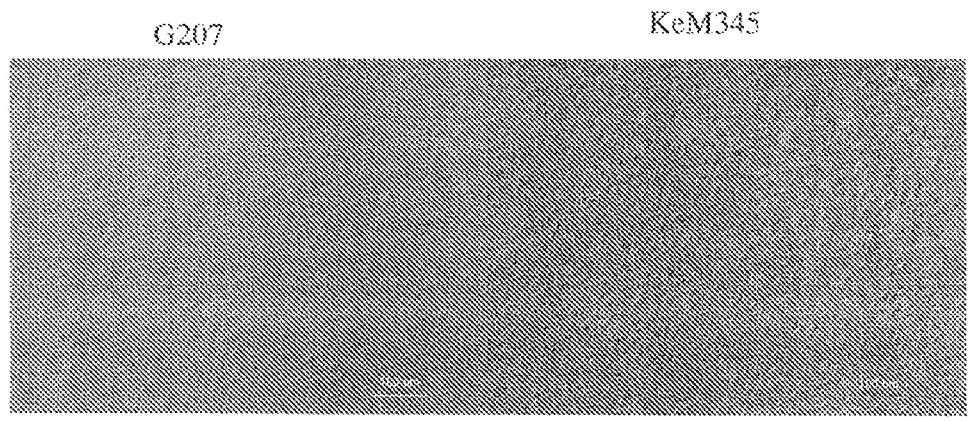
[Fig.12]
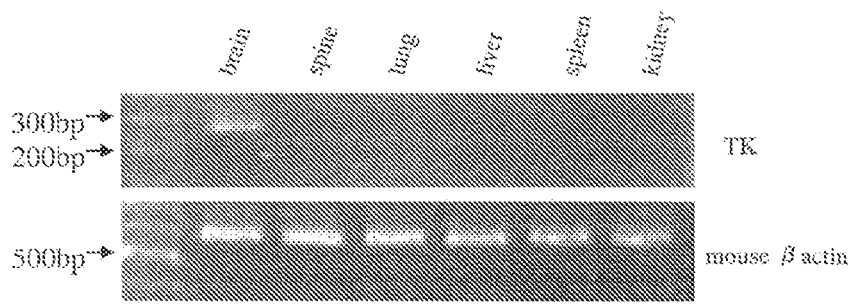
[Fig.13]
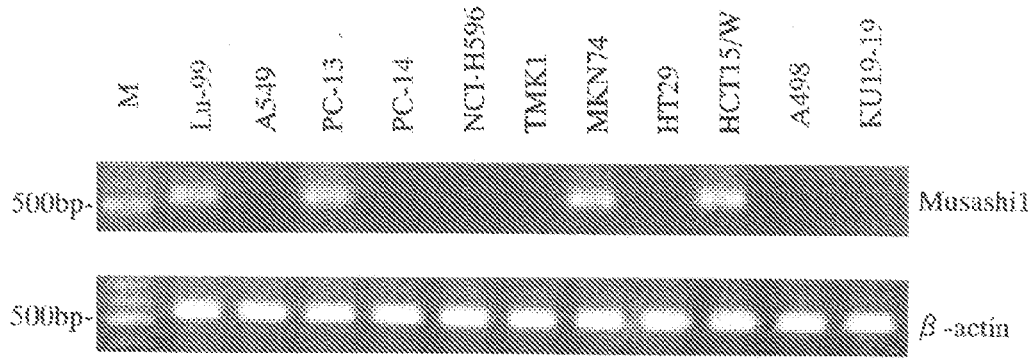

[Fig.14]
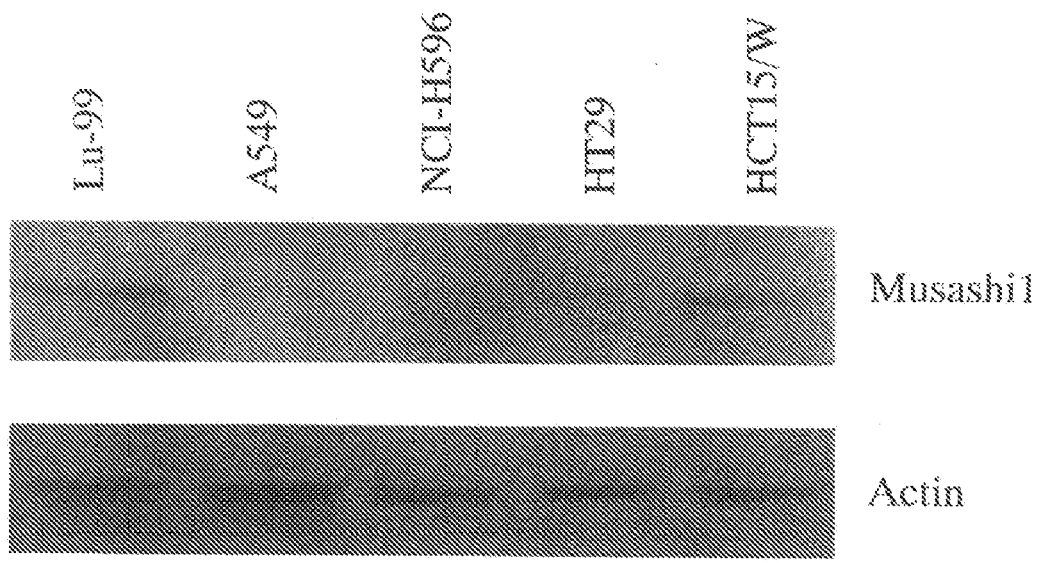
[Fig.15]
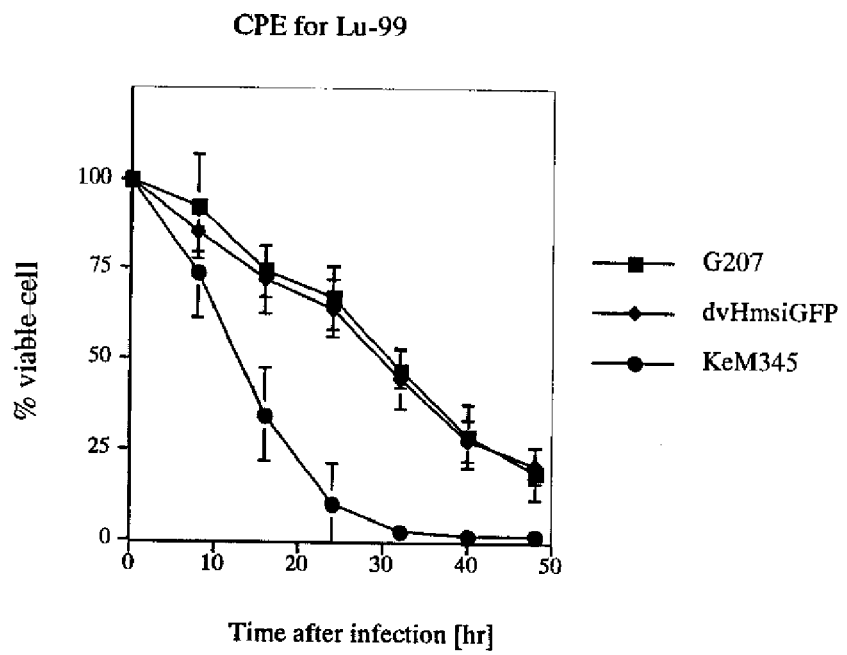

[Fig.16]
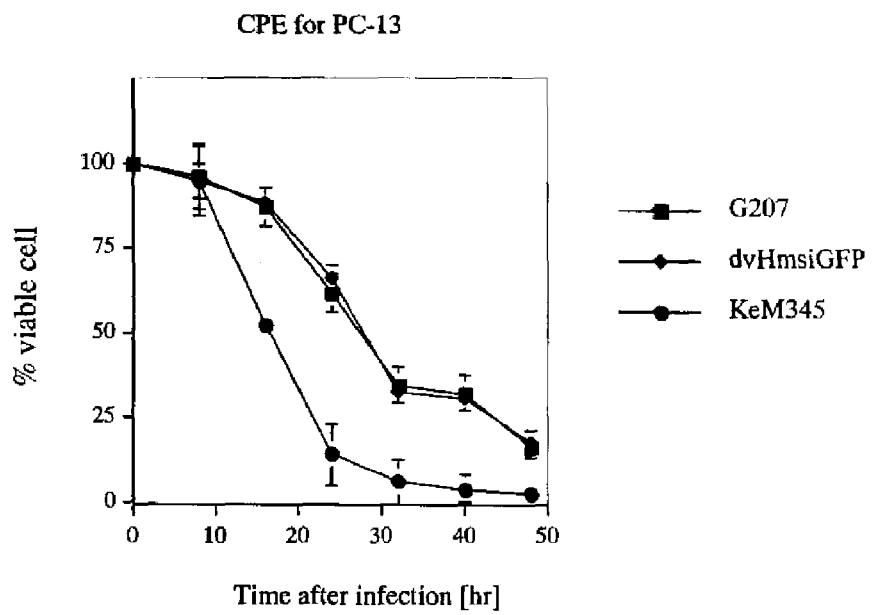
[Fig.17]
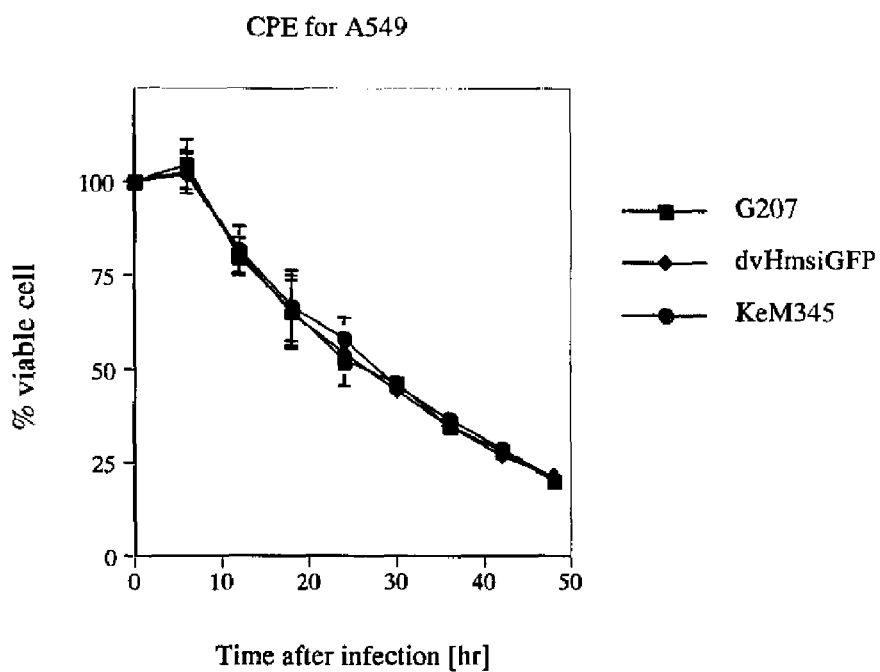

[Fig.18]
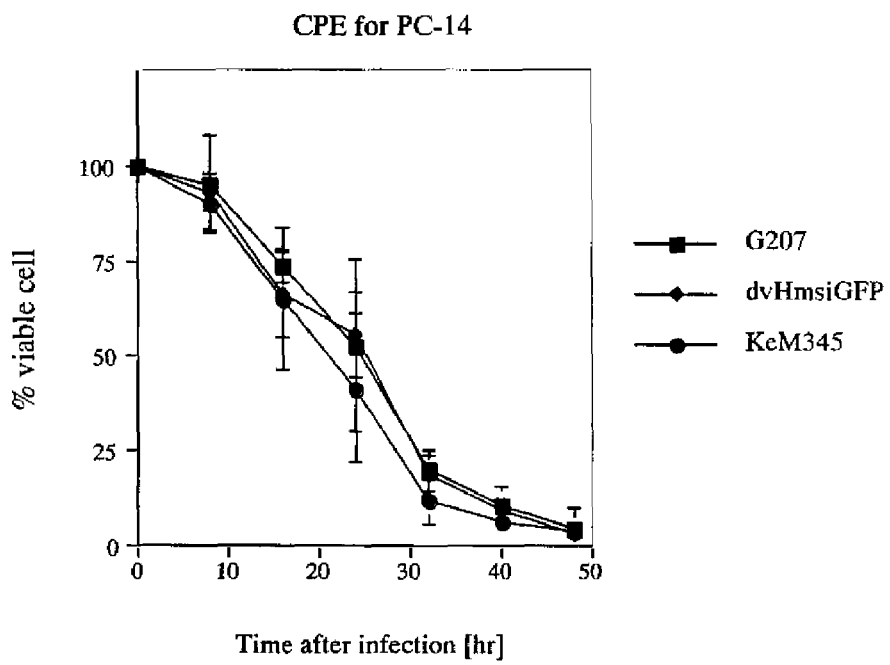
[Fig.19]
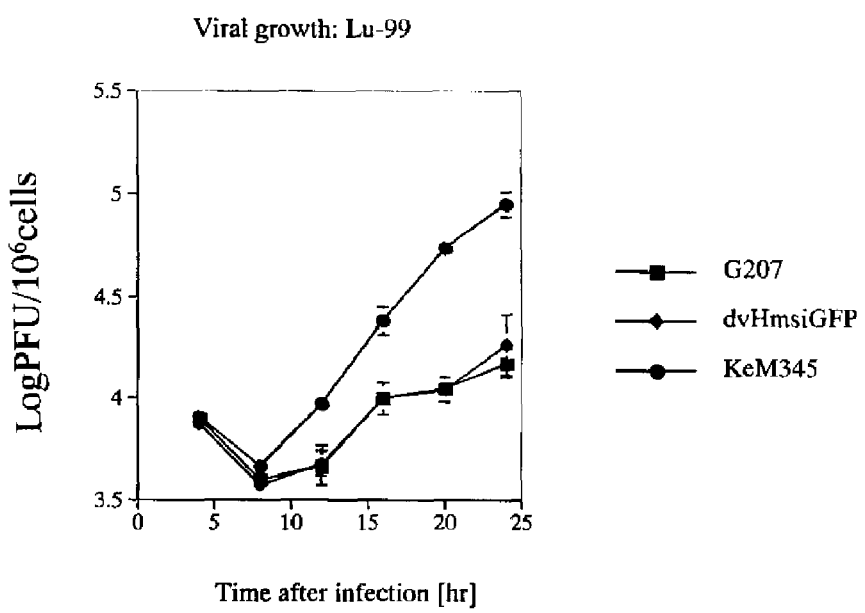

[Fig.20]
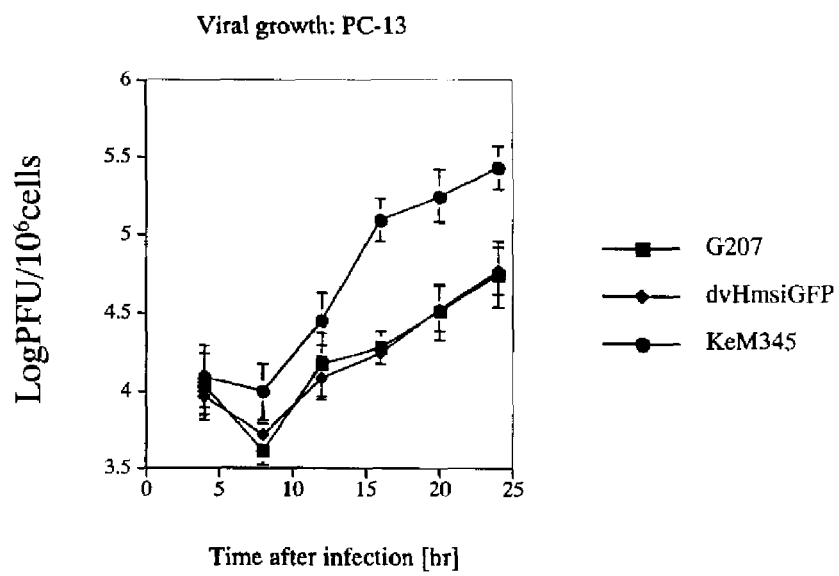
[Fig.21]
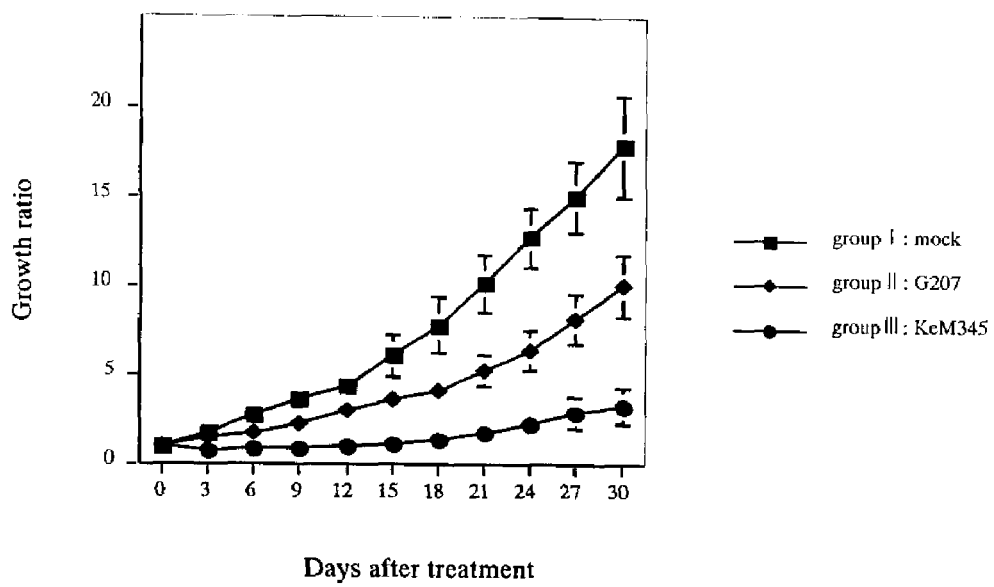

HSV WITH A MUSASHI PROMOTER REGULATING γ34.5 AND RIBONUCLEOTIDE REDUCTASE EXPRESSION

TECHNICAL FIELD

The present invention relates to a recombinant HSV useful for treating glioma such as human glioma using Musashi1 promoter. The present invention, more particularly, relates to a recombinant virus having a gene such as γ34.5 gene which is called as a neurovirulence factor and involved in the replication proliferation of HSV in tumor cells such as human glioma cells, and a viral DNA which has lost a function of expressing a gene product involved in the replication proliferation of the HSV.

BACKGROUND ART

Malignant glioma, in particular, polymorphism glioblastoma (GBM) is the most common and desperate form of the primary brain tumor of adults (for example, see Non-Patent Document 1). Since GBM tends to infiltrate widely into normal brain tissues in the periphery of GBM, it is virtually impossible to completely remove GBM even with the assistance of recent neural image processing techniques and improved surgical techniques. In the situation, another type of therapy has been required. However, despite great progress has been made in diagnostic procedure, radiation therapy, chemotherapy and supportive therapy, these neoplasms show strong resistance to the conventional therapies (for example, see Non-Patent Documents 2, 3, 4 and 5). The prognosis of the patients remains poor for the past 20 years. Most of the patients succumb to the disease within one year from the diagnosis (for example, see Non-Patent Documents 6 and 7). Since there are no effective therapies to be applied to the disease and patient's prognosis is extremely poor, options for a new therapy such as gene therapy must be offered.

Up to present, tumor transduction (gene introduction into a tumor) by means of a replication-defective vector has not yet been achieved with high efficiency. In the circumstances, a replication-competent virus vector is expected to serve as a cancer therapeutic agent (for example, see Non-Patent Documents 8, 9 and 10). The recent development in gene therapy for cancer has been made primarily on the use of an oncolytic virus, which not only delivers a cytotoxic gene to tumor cells but also directly disrupts the tumor cells through lytic-infection as well as designed so as to selectively replicate in the dividing cells by modifying the gene thereof (for example, see Non-Patent Documents 11 and 12). With respect to at least ten types of virus species, clinical tests have started (see Non-Patent Document 13). Use of an oncolytic virus designed so as to selectively replicate in dividing cells has been greatly expected from oncolytic activity and safety, since the effect of an anticancer agent injected to tumor mass can be anatomically enlarged by intraneoplastic replication and the oncogenic effect can be augmented by delivering an anticarcinogenic gene (for example, see Non-Patent Documents 14 and 15).

HSV is a double stranded virus, which has the longest genome (153 kb) of the DNA viruses proliferating within the nucleus and encodes 84 types of open reading frames. The genome is composed of an L (Long) region and an S (Short) region and having unique sequences each flanked by inverted repeat sequences. The entire base sequence of the virus genome has been determined and almost all functions of the genes of the virus have been elucidated. As an oncolytic mutant of HSV designed so as to selectively replicate in the dividing cells, two types of HSV mutants having a single gene mutated have been investigated. One of the mutants is a virus mutant, which has a defect in the function of the viral gene required for nucleic acid metabolism, such as thymidine kinase, ribonucleotide reductase (RR) or uracil N-glycosylate. The other one is a virus mutant, which has a defect in the function of γ34.5 (ICP34.5) gene serving as a virulence factor by increasing significantly the number of viruses released from an infected cell by inhibiting interrupt of protein synthesis of a host (for example, see Non-Patent Documents 16 and 17).

The HSV mutant having a single gene mutation has a risk of going back to a wild type through back mutation due to homologous replication or the like. Other than this, there are the following problems. For example, in a thymidine kinase function defective mutant, resistance to ganciclovir may increase. In a γ34.5 function defective mutant, oncolytic activity may decrease. In the circumstances, in order to reduce the risk of back mutation to a wild type, an HSV mutant having a plurality of mutations introduced therein has been developed. Examples of such an HSV mutant may include G207 and MGH1 defective in two functions: a γ34.5 defective mutation and a ribonucleotide reductase insertional mutation. When such a double mutant is directly injected to the skull, it replicates relatively selectively in tumor cells compared to normal tissue cells while significantly decreasing neurovirulence and maintaining sensitivity to ganciclovir. Since such a double mutant HSV lineage maintains a defective γ34.5 gene, it is virulent to normal tissue but weak. Conversely, these mutants apparently show an oncolytic effect upon tumor cells; however, the oncolytic effect thereof is lower than that produced by a mutant having non-defective γ34.5 gene.

The mutant G207 was developed by Martuza et al. as a double mutant of herpes simplex virus type I (HSV-I) by introducing a deletion in the γ34.5 gene and inserting the LacZ gene into the ribonucleotide reductase (ICP6) gene (for example, see Non-Patent Document 18, Patent Document 1). The mutant G207 is superior to other viruses in view of therapy. The mutant G207 is reproduced in dividing cells, with the result that the infected cells causes cell lysis to die. However, the proliferation of G207 is significantly attenuated in non-dividing cells. When G207 is injected into a tumor established in an athymic mouse, growth of the tumor is suppressed by tumor specific replication. As a result, the life of the mouse is prolonged (for example, see Non-Patent Document 19). Furthermore, when G207 is injected into a tumor in an immune responsive mouse, a tumor specific immune response is induced, with the result that proliferation of a tumor in which G207 is not injected therein is also suppressed (for example, see Non-Patent Document 20). In this case, G207 serves as an in-situ cancer vaccine. Up to present, gene therapy using mutant herpes virus G207 has been applied primarily to brain tumors and clinical application of G207 has been started in the United State (for example, see Non-Patent Document 9). In the clinical application, the safety of G207 has been proven; however, it has been reported that G207 is not so effective according to the clinical results so far reported (for example, see Non-Patent Documents 9 and 10).

When a viral vector is constructed for clinical application, the viral vector must have both safety and oncolytic efficacy (for example, see Non-Patent Documents 21 and 22). The safety varies directly depends upon the replication selectiveness of a virus mutant, whereas the efficacy varies depending upon the ability of the virus to effectively transmit tumor cells and proliferate in the neoplastic mass infected. An HSV vector having a plurality of mutations, such as G207, has been constructed with effort in an attempt to improve safety and reduce the risk of back mutation to a wide type. However, their oncolytic efficacy seems to decrease, at the same time. One of defective genes in G207 is γ34.5 gene, which is also called a neurovirulence factor. The γ34.5 gene has a role in significantly increasing the number of viral cells released from an infected cell (host) by inhibiting interrupt of host protein synthesis (for example, see Non-Patent Documents 16 and 23). G207 is greatly improved in safety by deleting the γ34.5 gene; however, it seems that the therapeutic effect has slightly decreased.

Several strategies are known to construct an HSV selectively replicating in a tumor cell. For example, mention may be made of making a deletion or mutation of a virus gene required for replication of a division-completed cell (for example, see Non-Patent Documents 12, 14 and 24); making a deletion of a virus gene responsible for regulating production of viral progenies (for example, see Non-Patent Documents 25, 26 and 27); using a tumor specific promoter for regulating expression of an indispensable virus gene (for example, see Non-Patent Document 28); modifying receptor specificity of a HSV glycoprotein to a tumor rather than normal tissues (for example, see Non-Patent Document 29), and so forth.

Musashi1 is a neural RNA binding protein found by the present inventors and is an evolutionally well conserved marker for a neural stem cell/precursor cell (for example, see Non-Patent Documents 30, 31, 32 and 33). Musashi1 has a high possibility of playing a crucial role in post-transcriptional gene regulation, which is essential for proper development of neural cells and glia cells (for example, see Non-Patent Documents 30, 31, 32, 33 and 34). Recent studies have elucidated that Musashi1 is expressed in a plurality of tumors, especially, a malignant glioma in the central nerve system (for example, see Non-Patent Documents 35, 36 and 37) and can be used as a marker for a malignant glioma (for example, see Non-Patent Documents 36 and 37). Other studies have reported that the mouse Musashi1 promoter (P/Musashi1) works in the human fetus brain, and that neural stem cells can be screened by a fluorescence activated cell sorter (FACS) based on GFP expression driven by P/Musashi1 (for example, see Non-Patent Document 38).

As is described above, clinical tests of an oncolytic virus therapy using HSV-G207 for glioma are carrying out in the United States. The safety of HSV-G207 has been demonstrated; however, the therapeutic effect has not yet been proved. This is conceivably because G207 is attenuated, leading to a replication attenuation type. Then, the present inventors came up with an idea that if the γ34.5 gene inactivated in G207 is reproduced in a glioma alone by use of the Musashi1 promoter selectively working in the glioma, stronger therapeutic effect can be exerted. Then, they developed an amplicon vector expressing γ34.5 by the Musashi1 promoter (Patent Document 2). However, since a process for producing the amplicon vector is complicated, it was difficult to obtain a stable amplicon vector. Thus, it was not easy to put it into clinical use.

Patent Document 1: U.S. Pat. No. 5,585,096

Patent Document 2: Japanese Patent Laid-Open No. 2005-73653

Non-Patent Document 1: Benign Cerebral Gliomas, Vol. 1. pp. 181-189, 1995

Non-Patent Document 2: Hum. Gene Ther. 8, 965-977, 1997

Non-Patent Document 3: Pathol. Res. Pract. 194, 149-155,

Non-Patent Document 4: Proc. Natl. Acad. Sci. U.S.A. 95, 14453-14458, 1998

Non-Patent Document 5: J. Neurooncol. 42, 95-102, 1999

Non-Patent Document 6: J. Neurosurg. 88, 1-10, 1998

Non-Patent Document 7: Cancer Res. 62, 756-763, 2002

Non-Patent Document 8: Nat. Med. 6,879-885, 2000

Non-Patent Document 9: Gene Ther. 7,867-874, 2000

Non-Patent Document 10: Gene Ther. 7,859-866, 2000

Non-Patent Document 11: Surg. Oncol. Clin. N. Am. 7, 589-602, 1998

Non-Patent Document 12: Science 252, 854-856, 1991

Non-Patent Document 13: Nat. Med. 7, 781-787, 2001

Non-Patent Document 14: Hum. Gene. Ther. 5, 183-191, 1994

Non-Patent Document 15: Cancer Res. 58, 5731-5737, 1998

Non-Patent Document 16: Proc. Natl. Acad. Sci. U.S.A. 89, 3266-3270, 1992

Non-Patent Document 17: Nat Cell Biol 3, 745-750, 2001

Non-Patent Document 18: Nat. Med. 1, 938-943, 1995

Non-Patent Document 19: Cancer. Res. 55, 4752, 1995

Non-Patent Document 20: Hum. Gene Ther. 9, 2177-2185, 1998

Non-Patent Document 21: J. Virol. 73, 3843-3853, 1999

Non-Patent Document 22: J. Virol. 74, 4765-4775, 2000

Non-Patent Document 23: Science 250, 1262-1266, 1990

Non-Patent Document 24: Hum. Gene Ther. 8, 533-544, 1997

Non-Patent Document 25: Neurosurgery 32, 597-603, 1993

Non-Patent Document 26: Proc. Natl. Acad. Sci. USA 92, 1411-1415, 1995

Non-Patent Document 27: Lab. Investig. 73, 636-648, 1995

Non-Patent Document 28: J. Virol. 73, 7556-7564, 1999

Non-Patent Document 29: J. Virol. 72, 9683-9697, 1998

Non-Patent Document 30: Neuron 13, 67-81, 1994

Non-Patent Document 31: Dev. Biol. 176, 230-242, 1996

Non-Patent Document 32: Genomics 52, 382-384, 1998

Non-Patent Document 33: Dev. Neurosci. 22, 139-153, 2000

Non-Patent Document 34: J. Neurosci. 17, 8300-8312, 1997

Non-Patent Document 35: Differentiation. 68, 141-152, 2001

Non-Patent Document 36: BBRC 293, 150-154, 2002

Non-Patent Document 37: GLIA 34, 1-7, 2001

Non-Patent Document 38: Nat. Biotechnol. 19, 843-850, 2001

DISCLOSURE OF THE INVENTION

Object to be Solved by the Present Invention

Conventionally, malignant brain tumor, in particular, glioblastoma, is usually treated by surgical removal, irradiation and administration of anticancer agent as standard therapies. However, prognosis is significantly poor. Thus, development of a novel therapy is urgently required. It is difficult to remove the tumor in its entirety by a surgical operation. The response rate of a tumor to irradiation is low. In the chemotherapy, since a drug resistance mechanism functions, the effect is low.

An object of the present invention resides in providing a recombinant HSV, which has an ability to specifically kill tumor cells such as human glioma cells in vivo, is useful and safe for treating human glioma and easily put in clinical use, and resides in providing a therapeutic drug for human glioma etc., containing the aforementioned recombinant HSV as an active ingredient.

Means to Solve the Object

The present inventors considered as follows. To construct a clinically applicable HSV vector, it is important to enhance oncolytic efficacy of a conventional mutant without decreasing the safety as much as possible. Then, they studied on several strategies for allowing HSV to replicate selectively in tumor cells. Of them, they thought that use of a tumor specific promoter would be promising for regulating expression of an indispensable gene.

On the other hand, mutant G207 of herpes simplex virus type I (HSV-I) is constructed by deleting a part of the γ34.5 gene and inserting the lacZ gene into ribonucleotide reductase (UL39) gene, as described above. Since these genes are inactivated in this manner, the mutant G207 loses the functions of expressing γ34.5 and ribonucleotide reductase. G207 shows efficient oncolytic activity according to in vitro and in vivo studies; but it shows minimum toxicity in normal tissue. Clinical tests of G207 to malignant glioma are now carrying out. However, according to the results of a phase-I test, it was demonstrated that G207 has a safety; however, the results that G207 has efficient oncolytic activity were not obtained. The safety of G207 was very much improved by deleting the γ34.5 gene encoding a neurovirulence factor; however, oncolytic activity by HSV1 significantly decreased. The present inventors took a thought for the decrease in oncolytic activity of G207 and came up with an idea that if the γ34.5 gene is specifically expressed only in tumor cells, therapeutic effect would increase more than the case where γ34.5 is not expressed.

The present inventors took a thought for enhancing therapeutic effect of G207 without decreasing the safety thereof. They came up with an idea that Musashi1 promoter (P/Musashi1), which is a neural RNA binding protein found by the present inventors, and has recently been elucidated to be expressed in a human malignant glioma and used as its marker, can act upon a malignant glioma other than neural precursor cells, in particular, can be used as a tumor specific promoter for regulating expression of the HSV1 gene involved in replication proliferation of HSV in a malignant glioma. Then, at first, they analyzed expression of Musashi1 mRNA by RT-PCR in human glioma cell lines (U87MG, U251, T98G) and other several cancer cell lines (lung cancer cell line A549, gastric cancer cell line TMK-1, colon cancer cell line HT29, bladder cancer cell lines KU19-9 and T24 and prostate cancer cell line DU145). As a result, they confirmed that mRNA of Musashi1 is expressed specifically in a glioma cell line and a neuroblastoma cell line out of the tumor cell lines. The results completely agreed with the cases so far reported (Differentiation 68, 141-152, 2001, GLIA 34, 1-7, 2001). As a second step, they investigated on transcriptional activity of P/Musashi1, which is known to work in the neural stem cells of a human fetus brain (Nat. Biotechnol. 19, 843-850, 2001). Furthermore, they investigated on transcriptional activity of P/Musashi1 in the human glioma cell line and other several tumor cell lines by GFP reporter assay. As a result, they obtained data indicating that the transcriptional activity of P/Musashi1 is significantly high in the human glioma cell line compared to the other several tumor cell lines. From the results, the present inventors confirmed that P/Musashi1 works selectively in the human glioma cell line.

Next, the present inventors came up with an idea of retargeting, which is a method of transcribing the γ34.5 gene (which is an HSV1 gene involved in replication proliferation of HSV) by P/Musashi1. They thought that the retargeting possibly provides a means for attaining virulence exhibiting selectively in a glioma while maintaining attenuated virulence in normal tissues. Then, they prepared a replication defective virus by regulating transcription of the γ34.5 gene by P/Musashi1. The replication defective virus thus prepared and G207 serving as a helpes virus were co-transfected to a glioma cell to obtain dvM345 and used as a virus stock. The dvM345 (virus stock) was found to exhibit significantly high cytopathic efficacy in a human glioma cell line compared to the case where G207 alone was used in culture. In contrast, no distinguishable difference was observed between dvM345 and G207 alone in the other cancer cell lines. In addition, according to the results of single-step virus growth analysis, it was found that dvM345 produces a large number of progeny viruses (G207) in human glioma cell line, U87MG, in which P/Musashi1 efficiently works. This means that dvM345 provides high oncolytic activity. However, in lung cancer cell line A549, in which P/Musashi1 fails to work efficiently, no such an effect was obtained. From these, it was confirmed that the high oncolytic activity of dvM345 is expressed specifically in a tumor. However, in lung cancer cell lines Lu-99 and PC-13, in which P/Musashi1 effectively works, production of KeM345 progeny viruses increased.

Next, using two nude mouse models: a subcutaneous U87MG tumor model and an intracerebral U87MG tumor model, in vivo therapeutic effect of dvM345 was investigated. In the subcutaneous tumor model, dvM345 drastically inhibited growth of U87MG tumor compared to G207 alone. In the intracerebral U87M tumor model, an animal group treated with a low dose ($5.0 \times 10^5$ PFU) of G207 viruses was compared to an animal group treated with dvM345. As a result, the latter one shows a statistically significant increase in survival-rate. As is apparent from the investigation in both models, therapeutic effect increased by injecting dvM345 (virus stock) directly into a tumor. On the other hand, the present inventors investigated on the safety of dvM345 using 3 mice. No side effect was observed in a dose of $5.0 \times 10^6$ PFU.

Furthermore, as long as the safety of a mutant virus is concerned, the safety varies directly dependent upon selectivity of virus replication, as mentioned above. Likewise, when a tumor specific promoter P/Musashi1 is used, the major problem directly depends upon the specificity of the promoter. In light of the nature of Musashi1 (Dev. Biol. 176, 230-242, 1996, J. Neurosci. 17, 8300-8312, 1997, Genomics 52, 382-384, 1998, and Dev. Neurosci. 22, 139-153, 2000), which is a neural RNA binding protein and is preferentially expressed in primitive and undifferentiated CNS cells, it has been estimated that the promoter may not work in peripheral differentiated normal tissues. However, other that the activity as neural precursor cells of P/Musashi1 that has been first reported by the present inventors (Nat. Biotechnol. 19, 843-850, 2001), and it can also be called as glioma specific promoter. As is mentioned above, the present inventors prepared dvM345 using P/Musashi1 and expressed γ34.5 in a glioma specific manner. As a result, they found out that the therapeutic effect of G207 can be augmented without damaging the safety thereof (Patent Document 2).

However, when dvM345 (virus stock) is used, there is a problem. Compared to use of G207 alone, dvM345 maintains a toxic profile characterized by exhibiting higher oncolytic activity in vitro and in vivo while maintaining preferable safety. However, a vector must be prepared by using an amplicon plasmid and a helper virus every time dvM345 is produced. For this reason, clinical application of dvM345 was not easy. Then, the present inventors constructed a novel recombinant HSV named KeM345 by means of a genetic recombination technique. More specifically, KeM345 was prepared by inserting a γ34.5 gene transcription unit, which is expressed by Musashi1 promoter, by means of homologous recombination into a ribonucleotide reductase gene site of the genome of herpes simplex virus (HSV) G207 previously attenuated. The KeM345 was obtained as a purified strain. The present inventors found that the purified KeM345 was a recombinant virus itself (back to a deletion mutant lacking only ICP6). Therefore, the obtained virus KeM345 not only proliferates by infecting cultured cells with the virus but also exhibits unexpectedly and extremely excellent cytotoxicity (cytolytic ability) selectively to a malignant glioma compared to that of dvM345 (virus stock). The replication of the virus corresponded to that of wild type HSV. Based on these findings, the present invention was accomplished.

More specifically, the present invention relates to: ("1") A recombinant HSV comprising:

Musashi1 promoter, a gene involved in HSV replication proliferation and ligated downstream of the Musashi1 promoter, a poly A sequence terminating transcription of the gene performed by the Musashi1 promoter, and a viral DNA which has lost a function of expressing a gene product involved in replication proliferation of HSV by inactivation of the gene involved in replication proliferation of HSV by destruction, deletion or replacement thereof; ("2") The recombinant HSV according to ("1"), wherein the gene involved in HSV replication proliferation and ligated downstream of the Musashi1 promoter is γ34.5 gene of HSV; ("3") The recombinant HSV according to ("1") or ("2"), wherein the gene product involved in HSV replication proliferation includes γ34.5 and ribonucleotide reductase of HSV; and ("4") The recombinant HSV according to any one of ("1") to ("3"), wherein the recombinant HSV is a recombinant HSV, KeM345, which is obtained by inserting a γ34.5 gene transcription unit, which is expressed by the Musashi1 promoter, into a herpes simplex virus (HSV) genome previously attenuated (for example into a ribonucleotide reductase gene site of a herpes simplex virus type 1 (HSV-1) double mutation virus genome, by making a deletion in the γ34.5 gene and inserting the lacZ gene into the ribonucleotide reductase (ICP6) gene by homologous recombination).

The present invention further relates to: ("5") A therapeutic drug for a tumor in which Musashi1 is expressed, containing the recombinant HSV according to any one of ("1") to ("4") as an active ingredient; and (6) The therapeutic drug according to ("5"), wherein the tumor in which Musashi1 is expressed is a human glioma.

BRIEF DESCRIPTION OF DRAWINGS

FIG. 1 is a gel electrophoregram showing the results of Southern blot analysis of the recombinant virus KeM345 of the present invention.

FIG. 2 shows graphs indicating the results of oncolytic effect of the recombinant virus KeM345 of the present invention upon human derived glioma cell lines (U87MG, U87E6).

FIG. 3 shows graphs indicating the results of oncolytic effect of the recombinant virus KeM345 of the present invention upon human derived glioma cell lines (U251, T98G).

FIG. 4 shows a graph indicating the results of oncolytic effect of the recombinant virus KeM345 of the present invention upon neuroblastoma SK-N-SH.

FIG. 5 shows graphs indicating the results of oncolytic effect of the recombinant virus KeM345 of the present invention upon lung cancer cell line A549 and colon cancer cell line HT29.

FIG. 6 is a graph showing the results of single-step viral growth of the recombinant virus KeM345 of the present invention in a human glioma-derived cell line.

FIG. 7 is a diagram showing that P/Musashi1 efficiently works and expresses γ34.5 in the recombinant virus KeM345 of the present invention.

FIG. 8 is a graph showing growth inhibition effect of the recombinant virus KeM345 of the present invention upon a subcutaneous tumor.

FIG. 9 is a graph showing life extension effect of the recombinant virus KeM345 of the present invention upon an intracerebral tumor.

FIG. 10 is a graph showing that the life extension effect of the recombinant virus KeM345 of the present invention upon an intracerebral tumor is superior to that of dvM345.

FIG. 11 shows that a high HSV distribution is confirmed in a mouse tumor treated with the recombinant virus KeM345 of the present invention.

FIG. 12 shows the evaluation results on safety of the recombinant virus KeM345 of the present invention.

FIG. 13 shows the analysis results on the expression of Musashi1 mRNA in various types of human-derived tumor cell lines.

FIG. 14 is a gel electrophoregram showing the results of Western blot analysis of various human-derived tumor cell lines positive or negative for expression of Musashi1 mRNA.

FIG. 15 is a graph showing the oncolytic effect of the recombinant virus KeM345 of the present invention upon a human derived non-parvicellular lung cancer cell line (Lu-99).

FIG. 16 is a graph showing the oncolytic effect of the recombinant virus KeM345 of the present invention upon a human derived non-parvicellular lung cancer cell line (PC-13).

FIG. 17 is a graph showing the oncolytic effect of the recombinant virus KeM345 of the present invention upon a human derived non-parvicellular lung cancer cell line (A549).

FIG. 18 is a graph showing the oncolytic effect of the recombinant virus KeM345 of the present invention upon a human derived non-parvicellular lung cancer cell line (PC-14).

FIG. 19 is a graph of the results of single step viral growth of the recombinant virus KeM345 of the present invention in a non-parvicellular lung cancer cell line (Lu-99).

FIG. 20 is a graph of the results of single step viral growth of the recombinant virus KeM345 of the present invention in a non-parvicellular lung cancer cell line (PC-13).

FIG. 21 is a graph showing growth inhibition effect of the recombinant virus KeM345 of the present invention upon a subcutaneous tumor derived from a non-parvicellular lung cancer cell line.

BEST MODE OF CARRYING OUT THE INVENTION

As a recombinant HSV according to the present invention, any recombinant HSV may be used as long as it comprises Musashi1 promoter, a gene involved in HSV replication proliferation and ligated downstream of the Musashi1 promoter, a poly A sequence terminating transcription of the gene performed by the Musashi1 promoter, and a viral DNA which has lost a function of expressing a gene product involved in replication proliferation of HSV by inactivation of the gene involved in replication proliferation of HSV by destruction, deletion or replacement thereof. Examples of the gene involved in HSV replication proliferation include γ34.5 gene, ribonucleotide reductase (ICP6) gene, ICP0 gene, ICP4 gene and ICP27 gene of HSV. To satisfy both oncolytic activity and safety, the γ34.5 gene of HSV is preferable. More preferably, as an example of the gene involved in HSV replication proliferation and ligated downstream of the Musashi1 promoter, the γ34.5 gene of HSV may be exemplified. As an example of the gene product involved in replication proliferation of HSV, γ34.5 and ribonucleotide reductase of HSV may be mentioned, more specifically, a recombinant virus KeM345 may be exemplified. Recombinant virus KeM345 is a novel recombinant HSV obtained by inserting a γ34.5 gene transcription unit, which is expressed by the Musashi1 promoter, into a ribonucleotide reductase gene site of the genome of herpes simplex virus (HSV) G207 previously attenuated by means of homologous recombination. As the type of HSV, HSV1 and HSV2 may be exemplified.

P/Musashi1 to be used for producing the recombinant HSV of the present invention can be prepared in accordance with the method described previously (Nat. Biotechnol, 19, 843-850, 2001). The poly A sequence terminating transcription is not particularly limited as long as it is a poly A sequence derived from a mammal. For example, poly A sequences such as rabbit β-globin, SV40 and BGH may be exemplified. The gene transcription unit involved in replication proliferation of HSV expressed by Musashi1 promoter can be prepared in accordance with a customary method. Furthermore, the viral DNA which has lost a function of expressing a gene product involved in replication proliferation of HSV by inactivation of the gene involved in replication proliferation of HSV by destruction, deletion or replacement thereof, is not particularly limited, as long as it is a mutated genomic DNA of HSV, which is obtained by inactivating the same gene as the gene involved in replication proliferation of HSV used for producing the gene transcription unit. Specific examples thereof include the followings:

R3616 and 1716, which has lost a function of expressing γ34.5 involved in replication proliferation of HSV by inactivating the γ34.5 gene;

hrR3, which has lost a function of expressing ribonucleotide reductase involved in replication proliferation of HSV by inactivating the ribonucleotide reductase (ICP6) gene;

G207, which has lost functions of expressing γ34.5 and ribonucleotide reductase; and d120, which has lost replication proliferation ability of HSV by inactivating the ICP4 gene.

These mutated genomic DNAs of HSV can be prepared by the methods described previously; specifically, R3616, by the method described in Science, 250, 1262-1266, 1990; 1716 by the method described in Gene Ther, 7, 859-866, 2000; hrR3 by the method in J Virol, 62, 196-205, 1988; and G207 by the methods described in Nat. Med. 1, 938-943, 1995 and U.S. Pat. No. 5,585,096.

The recombinant HSV of the present invention can be constructed by co-transmitting the aforementioned gene transcription unit linearized and the mutated genomic DNA of HSV to a host cell, thereby inserting the gene transcription unit into the mutated genomic DNA of HSV by means of homologous recombination. The recombinant HSV of the present invention may be present in the form of liquid, a frozen product thereof, or lyophilized powder thereof. Alternatively, the recombinant HSV may be present in form of a frozen product of a host cell in a prophase state.

The host cell to be used for preparing the recombinant HSV of the present invention is not particularly limited as long as it is a cell in which homologous recombination takes place when the gene transcription unit linearized and the mutated genomic DNA of HSV are co-transmitted to the cell, thereby providing a recombinant HSV. For example, a mammalian cell that may possibly serve as a host cell of HSV may be mentioned. Furthermore, as the cell that can be infected with the recombinant HSV of the present invention, a tumor cell, in which P/Musashi1 specifically works, can be preferably mentioned. Specific examples thereof include human glioma cells and undifferentiated neuro-epithelial tumor cells such as neuroblastoma. Examples of the human glioma cells include human glioma cell lines such as U87MG, U251 and T98G and tumor cells isolated from human glioma tissues.

As the therapeutic drug for a tumor in which Musashi1 is expressed, any therapeutic drug may be used as long as it contains the recombinant HSV of the present invention. Examples to the tumor in which Musashi1 is expressed include, other than a human glioma, undifferentiated neuro-epithelial tumor such as neuroblastoma and a certain type of non-parvicellular lung cancer, for convenience sake. Accordingly, as a representative therapeutic drug according to the present invention, a therapeutic drug for human glioma may be mentioned. Furthermore, as a therapeutic method using the therapeutic drug for human glioma, examples include a method of directly administering the therapeutic drug for human glioma to a human glioma. When the glioma therapeutic drug is used, for example, as a pharmaceutical product, it may contain a general and pharmaceutically acceptable carrier and various additives for a preparation such as a binder, stabilizer, diluent, excipient, pH buffer, disintegrator, solubilizer, auxiliary solubilizer and isotonic agent. These therapeutic drugs may be administered orally or parenterally. More specifically, the therapeutic drugs may be administered orally in dosage form such as powder, granule, capsule, syrup and suspension. Alternatively, the therapeutic drugs may be administered parenterally in injection form such as a solution, emulsion or suspension. The therapeutic drugs may be administered intranasally in the form of spray. However, the therapeutic drugs are preferably injected directly into a tumor tissue such as a human glioma, as the drug may immediately induce tumor lysis.

The present invention will be explained more specifically by way of examples; however, the technical scope of the present invention is not limited to these exemplifications. Note that human glioma cell lines (U87MG, U251 and T98G), human neuroblastoma cell line SK-N-SH, human-derived lung cancer cell line (A549), human-derived colon cancer cell line (HT29) and African green monkey renal cells (Vero cells) were obtained from the American Type Culture Collection. Cell lines SK-N-SH, A549, and Vero cells were cultured in Dulbecco's modified Eagle's medium (DMEM) supplemented with 10% heat-inactivated fetus bovine serum (IFBS). Cell line HT29 was cultured in RPMI1640 medium supplemented with 10% IFBS. All cell lines each were maintained in a medium containing an antibiotic (manufactured by Sigma) at 37° C. in a humidified atmosphere containing 5% carbon dioxide and usually subcultured every two weeks by use of a 0.25% trypsin-ethylenediamine tetraacetate solution (manufactured by Sigma).

EXAMPLE 1

Preparation of Recombinant Virus KeM345

(Homologous Recombination)

Amplicon plasmid pSRaP/Musashi1: the γ34.5 gene (Kanai R et al. Gene Ther; advance online publication, Sep.

15, 2005; doi: 10. 1038/sj.gt. 3302636/Japanese Patent Laid-Open No. 2005-73653) was digested with restriction enzyme XbaI. Fragments of about 5 Kb having blunt ends were recovered and used as insert fragments (inserts). Each of the inserts has P/Musashi1, a full-length γ34.5 sequence and a BGH-polyA sequence which were ligated downstream of P/Musashi1. Subsequently, plasmid pKX2βG3 (Mineta et al. Nat Med, 1995; 1: 938-943) was digested with NdeI and EcoRV to obtain fragments with blunt ends. To each of these fragments, the insert was introduced and ligated to obtain plasmid pKX-P/Musashi1:γ34.5. Plasmid pKX-P/Musashi1:γ34.5 was then digested with restriction enzyme HindIII to obtain a linearized plasmid thereof. The linearized plasmid and viral DNA of G207 were introduced into a Vero cell by co-transfection in accordance with the Lipofection method (using Lipofectamine 2000, manufactured by in vitrogen Corporation). The preparation of viral DNA was performed in the same manner as in the method of Mineta et al. (Nat Med, 1995; 1: 938-943). About 4 days later, viruses grown were once recovered and introduced into human neuroblastoma cell line SK-N-SH by infection. Further one day after the infection and after cytotoxic effect was confirmed, viruses were recovered, and then, introduced by infection into single-layer Vero cells confluently grown in a 10 cm dish. About 18 hours after the infection, an X-gal-containing agarose was overlayed on the single-layer Vero cells and allowed to grow for further one day. The emergent plaques were observed under an optical microscope to distinguish white plaques from blue plaques. White plaques alone were recovered and introduced into Vero cells grown in a 24 well plate by infection. When viruses generated, they were again introduced by infection into single-layer Vero cells grown confluently in a 10 cm dish. The resultant blue and white plaques were distinguished and white plaques alone were selected. The same procedure was repeatedly performed three times. Note that blue and white plaques are generated by the following reasons. Since a LacZ gene is inserted in G207, it produces a blue plaque by X-gal staining; however, a recombinant virus to be expected produces a white plaque since the insert is introduced within the LacZ gene site.

(Southern Blot)

It was confirmed whether the insert was properly introduced or not in a recombinant virus by Southern blot. Three types of probes were used. Plasmid pKX2βG3 was digested with restriction enzymes NdeI and EcoRV to obtain about 1.9 Kb fragments, which were used as LacZ probes. The remaining fragments were allowed to self-ligate to obtain plasmids, which were digested with restriction enzymes HindIII and XbaI to obtain fragments. These fragments were used as ICP6 probes. On the other hand, P/Musashi1 was digested with restriction enzyme XhoI to obtain 2.2 Kb fragments, which were used as P/Musashi1 probes. The viral DNAs of StrainF, hrR3, G207 and KeM345 were digested with restriction enzymes (XhoI, BamHI) and subjected to 1% agarose gel electrophoresis, transferred to a nylon membrane (Hybond-N+, manufactured by Amersham). Thereafter, using the aforementioned probes, Southern blot was performed. The labeling of probes and detection of signals were performed by use of ECL Random Prime Labelling and Detection Systems, Version II (manufactured by Amersham). As a result, it was confirmed that the insert was properly introduced into each of recombinant viruses) (FIG. 1).

EXAMPLE 2

Oncolytic Effect

Twenty four hours before infection with viruses, human derived-glioma cell lines (U87MG, U87E6, U251, T98G), human neuroblastoma cell line (SK-N-SH), human non-parvicellular lung cancer cell line (A549) and human colon cancer cell line (HT29 cells) were inoculated in individual 12-well plates in an amount of $2.0 \times 10^5$ cells. Infection of virus G207 or KeM345 was performed in PBS (0.3 ml) supplemented with 1% IFBS at an MOI of 0.01 plaque formation unit (PFU)/cell for 30 minutes. Furthermore, control cells were infected with an extract prepared from mock-infected cells in the same manner as in the virus infection process. The number of survival cells was determined by the trypan blue exclusion method, which was performed every 12 hours after the infection. The assays were all repeatedly performed three times. To check the feature of cytotoxicity of KeM345, examination was performed with respect to human derived-glioma cell lines (U87MG, U87E6, U251, T98G) and neuroblastoma cell line SK-N-SH, in which P/Musashi1 effectively works, and other cell lines in which P/Musashi1 fails to work effectively (A549 and HT29). Infection with viruses (G207 or KeM345) was performed at an MOI of 0.01. The results are shown in FIGS. 2 to 5. It was confirmed that the in vitro cytotoxic effects of KeM345 on human derived-glioma cell lines (U87MG, U87E6, U251, T98G) and neuroblastoma cell line (SK-N-SH), in which P/Musashi1 effectively works, are significantly higher than that of G207 (t-test, $p<0.01$). In addition, in the glioma cell lines, a cytopathic effect was observed 24 hours after infection with statistically significant difference between KeM345 and G207 ($p<0.05$, unpaired t-test). Also in cell line SK-N-SH, statistical significance was observed 60 hours onwards after infection. On the other hand, in the other tumor cell lines (A549 and HT29), no significant difference was observed in cytopathic effect between the viruses used in this study.

EXAMPLE 3

Single Step Viral Growth

To a 6-well plate, cells ($5.0 \times 10^5$) of each of cell types U87MG, U87E6, U251, T98G, SK-N-SH, A549 and HT29 were inoculated. Twenty four hours later, the cells were infected with viruses (R3616, G207, KeM345, StrainF). Viral infection was performed at an MOI of 0.01 in 0.5 ml of PBS supplemented with 1% IFBS for 30 minutes. Twenty four hours after infection, viruses were recovered from the wells and titration was performed. The number of plaques was counted and plaque-forming units per well (PFU/well) were calculated and indicated by Log PFU/well (FIG. 6). Experiments were all repeatedly performed three times. As a result, in human glioma derived cell line (U87MG, U87E6, U251, T98G), KeM345 produced a large number of progeny viruses ($p<0.05$, unpaired t-test) compared to G207, more specifically, produced about 100-fold of the progeny viruses of G207. The same results were obtained in SK-N-SH. In contrast, in the other cell lines (A549 and HT29), the amount of viral production of KeM345 was indistinguishable from that of G207 (unpaired t-test, $p<0.01$).

EXAMPLE 4

Function of P/Musashi1 Expressed Highly Efficiently in KeM345

In HSV infected cells, first, a virus-derived RNA is changed into double stranded RNA, and then, eukaryotic cell translation initiation factor 2α(eIF-2α) was phosphorylated, leading to termination of protein synthesis. Finally, proliferation of the virus is inhibited. γ34.5 is reported to dephosphorylate eIF-2α and thus never stops protein synthesis, thus promoting viral replication (Chou J, Roizman B. Proc Natl Acad Sci USA, 1992; 89: 3266-3270). Then, in order to biochemically support that KeM345 expresses γ34.5 only in a cell line in which P/Musashi1 efficiently works, Western blot was performed as follows. U87MG, U87E6 and A549 cells were grown sub-confluently in a 10 cm dish. Viruses (StrainF, R3616, G207, KeM345) were transmitted by infection to the cells at an MOI of 0.5. Fifteen hours after the infection, the cells were recovered. Then, proteins were extracted from the cells and subjected to Western blot analysis. SDS-PAGE was performed by loading 50 μg of protein per well. As antibodies, an anti-eIF2-α antibody (manufactured by Biosource) and an anti-phosphorylated eIF2-α (specific to phosphorylated site) (manufactured by Biosource) were used. As a control, an anti-actin antibody was used. A secondary antibody was allowed to react appropriately and detection was performed by the ECL detection Kit. As a result, in U87MG and U87E6 in which P/Musashi1 efficiently works, γ34.5 was expressed by infection of KeM345. From this, it was suggested that eIF-2α is dephosphorylated (FIG. 7).

EXAMPLE 5

Anti-Tumor Effect of Recombinant Virus KeM345 In Vivo (Animal Experiment)

Thymus-defective BALB/c female nude mice (nu/nu) of 6-week old, which were purchased from Japan SLC, Inc., were divided into groups consisting of 5 mice or 5 mice or less and raised in aseptic cages in such a manner that mice were free to take food and water (treated in an autoclave) at any time. Animals were all treated in accordance with the procedure approved by the Laboratory Animal Center (School of Medicine, Keio University). In the case of surgical operation, mice were anaesthetized by injecting peritoneally 0.25 ml of a solution, containing 84% bacteriostatic saline, 10% pentobarbital sodium (50 mg/ml; manufactured by Abbott Laboratories) and 6% ethanol, to each mouse. A researcher regularly made the rounds of the cages in order to check survival state of the mice.

(Model 1: Subcutaneous Tumor Model and Inoculation into a Neoplasm of the Subcutaneous Tumor)

U87E6 cells ($5.0 \times 10^6$ cells/50 μl) was subcutaneously injected into the right side of the abdomen of each BALB/c female nude mouse, thereby inducing a subcutaneous tumor. About 12 days after the implantation (inoculation) when the diameter of the subcutaneous tumor reached 6 mm, the mice were randomly divided into 3 groups (n=6 per group). G207 and KeM345 ($1.0 \times 10^6$ PFU) suspended in 20 μl virus buffer were respectively applied to each mouse of Group II and Group III, more specifically, applied within the neoplasm of each mouse. Mice of Group I serving as a control were treated with a mock infection extract (20 μl). The size of the tumor, more specifically, outer size thereof, was determined by a vernier caliper having a graduate of 0.1 mm or less. Based on bidemensional diameter measurements, the amount of tumor changed with time was obtained. The average growth rate of the tumor was determined by the following equation:

$$0.5(a \times b^2) \text{day n}/0.5(a \times b^2) \text{day}$$

(wherein a is the long axis, and b is the short axis). When the diameter of the tumor exceeded 24 mm, the animal was sacrificed. The statistical difference in growth rate between tumors was evaluated by the unpaired t-test ($p<0.01$). As a result, it was found that the tumor growth rate of the mouse group administered with KeM345 is significantly suppressed compared to those of the mouse groups administered with a mock infection extract and G207 (FIG. 8).

(Model 2: Intracerebral Tumor Model and Injection of Virus)

BALB/c female nude mice were anaesthetized and immobilized by a stereotaxis apparatus (manufactured by D. Kopf Instruments). Thereafter, the skin on the bregma was linearly cut to form a hole (1 mm) in the skull (at a site at 1.0 mm in the front side and 2.0 mm in the outer side from the bregma). U87E6 cells ($2.0 \times 10^5$ cells in 2 μl) was injected by use of a 5 μl-Hamilton syringe (manufactured by Hamilton Company) into the assigned site of the right frontal lobe of each of the nude mice. Twelve days later, the mice were randomly divided into 3 groups (n=10). G207 ($5.0 \times 10^5$ PFU), G207 ($1.0 \times 10^6$ PFU), KeM345 ($5.0 \times 10^5$ PFU), KeM345 ($1.0 \times 10^5$ PFU) and a mock infection extract (2 μl) were injected to mice of Group II, Group III, Group IV, Group V and Group I, respectively, at the assigned site having the same coordinations. The mice were continuously kept alive. The statistical difference between survival rates was evaluated by the Wilcoxon signed-ranks test ($p<0.01$). As a result, Groups IV and V exhibited a survival extension effect with statistical significance compared to Groups I to III. On the other hand, when Group IV and Group V (Kem345-administered groups) were compared, a dose-dependent effect was confirmed (FIG. 9).

(Model 3: Comparison of Survival Extension Effect Between dvM345 and KeM345)

To compare the effect of dvM345 to that of KeM345, U87MG cells ($2.5 \times 10^5$ cells), on which G207 exerted a poor effect, were implanted to the right frontal lobe of each of BALB/c female nude mice. Ten days after the implantation, viruses were administered into a tumor. As viruses, KeM345, dvM345, G207 and a mock infection extract were administered to mice (n=6 per group). The dose of viruses was set at $5.0 \times 10^5$ PFU, at which G207 produced virtually no effect. As a result, the KeM345-administered group exhibited significantly high survival extension effect compared to the dvM345-administered group (FIG. 10: Wilcoxson test, $p<0.01$).

EXAMPLE 6

Pathological Study

Seventeen days after implantation of U87E6 cells into BALB/c female nude mice, the mice were treated with G207 or KeM345 ($1.0 \times 10^6$ PFU). Five days after the treatment, the mice were sacrificed. Perfusion was performed in PBS containing 1% PFA and the mice were immobilized. Thereafter, the brain was removed. Specimens were fixed with 4% PFA at 4° C. for 24 hours or more. After treated with ethanol and xylene, each of the specimens was embedded in paraffin. In this manner, 4 μm-thick slide sections of the brain around the needle-tract were prepared. After paraffin was removed, immuno-staining was performed with an anti-HSV antibody (rabbit anti-HSV antibody, 1/200 dilution, manufactured by BETHYL laboratories) and a secondary antibody (biotinylated anti-rabbit IgG). Thereafter, contrast staining was performed with a hematoxylin solution and samples were observed by an automatic microscope (Eclipse-E1000, manufactured by Nikon Corporation). As a result, a high HSV distribution was observed in the group treated with KeM345 compared to the group (the cells) infected with G207 (FIG. 11).

EXAMPLE 7

Safety Evaluation for KeM345

After implantation of U87E6 cells into BALB/c female nude mice, KeM345 ($5.0 \times 10^6$ PFU) was injected into the right cerebral hemisphere of each mouse. Twenty eight days later, two mice were sacrificed and the brain, spine, lung, liver, spleen and kidney were removed and then DNA was recovered by DNAzol (manufactured by Invitrogen Corporation). Using the DNA as a template, it was examined whether DNA of HSV can be detected or not was in the same manner as in the method of Sundaresan P et al. (J virol 2000; 74: 3832-3841). DNA of HSV was detected by use of a primer pair of thymidine kinase (TK). A primer pair of mouse β-actin was used as an endogenic control (Morita A et al., Hepatol Res, 2003; 27: 143-150). As a result, it was found that β-actin (control) was expressed in all of the organs, whereas thymidine kinase was specifically expressed in the brain (FIG. 12).

EXAMPLE 8

Expression of Musashi1 mRNA in Various Types of Human Derived-Tumor Cell Lines RT-PCR analysis was performed to examine expression of Musashi1 mRNA in human derived-cancer cell lines (11 in total): five non-parvicellular lung cancer cell lines (Lu-99, A549, PC-13, PC-14, NCI-H596), two gastric cancer cell lines (TMK1, MKN74), two colon cancer cell lines (HT29, HCT15/W), one bladder cancer cell line (KU19-19) and one renal cell cancer cell line (A498). As an endogenic control, β-actin (551 bp) was used. As a result, the Musashi1 gene was expressed in two (Lu-99, PC-13) out of the five lung cancer cell lines, one (MKN74) out of the two gastric cancer cell lines and one (HCT15/W) of the two colon cancer cell lines. In contrast, no Musashi1 mRNA was detected in the other cell lines (FIG. 13).

EXAMPLE 9

Expression of Musashi1 Protein in Human Derived-Tumor Cell Line

Western blot analysis was performed with respect to lung cancer cell line Lu-99 and colon cancer cell line HCT15/W, which were positive for expression of Musashi1 mRNA, and two lung cancer cell lines A549 and NCI-H596 and the colon cancer cell line HT29, which were negative for expression of Musashi1 mRNA. Actin was used as an endogenic control. Musashi1 protein was detected at a molecular weight of about 40 kD in Lu-99 and HCT15/W, whereas it was not detected in the other cell lines (FIG. 14).

EXAMPLE 10

Oncolytic Effect in Human Derived Non-Parvicellular Lung Cancer Cell Line

According to the method described in Example 2, the oncolytic effect of HSV of the present invention in human derived non-parvicellular lung cancer cell lines was examined. Four types of human derived non-parvicellular lung cancer cell lines were used. More specifically, use was made of cell lines Lu-99 and PC-13, at which Musashi1 mRNA was detected in Example 8, and cell lines A549 and PC-14, at which Musashi1 mRNA was not detected. Virus KeM345 was transmitted. As controls, dvHmsil: GFP (replication-defective virus constructed by replacing γ34.5 of dvM345 with GFP) and G207 were used. These viruses were transmitted at a MOI of 0.1 based on the titer of herpes virus (G207). In the cell line in which P/Musashi1 effectively works, statistically significant cytopathic effect (P<0.05, unpaired t-test) was observed 16 hours after the infection with KeM345 virus, compared to the control virus (FIGS. 15 and 16). On the other hand, in the other cell lines, no difference was observed in cytopathic effect between the viruses (FIGS. 17 and 18).

EXAMPLE 11

Single-Step Viral Growth in Non-Parvicellular Lung Cancer Cell Line

To a 6-well plate, Musashi1-positive non-parvicellular lung cancer cell lines (Lu-99, PC-13, A549, PC-14) were inoculated in an amount of $5.0 \times 10^5$. Twenty four hours later, the cell lines were infected with viruses (G207, dvHmsil: GFP, KeM345). Viruses were transmitted at a MOI of 0.01 in 0.5 ml of PBS supplemented with 1% IFBS for 30 minutes. Titration was performed every 4 hours after the infection. The number of plaques was counted and plaque-forming units per well (PFU/well) were calculated and indicated by Log PFU/well. In Lu-99 and PC-13 in which P/Musashi1 effectively works, production of KeM345 progeny viruses increased (FIGS. 19 and 20). In A549 and PC-14 in which P/Musashi1 fails to effectively work, the same effect was not observed (data not shown).

EXAMPLE 12

Virus Inoculation to Subcutaneous Tumor Induced from Lung Cancer Cells

Lu-99 cells ($5.0 \times 10^6$ cells) was injected into the right side of the abdomen of each of BALB/c female nude mice in the same method as in Example 5, thereby inducing a subcutaneous tumor. The mice were divided into 3 groups (n=6 per group). G207 or KeM345 ($1.0 \times 10^7$ PFU each) was respectively applied to Group II mice and Group III mice, more specifically, applied within a neoplasm thereof. As a control, a mock infection extract was applied to Group I mice. When the size of a tumor exceeded 24 mm, the animal was sacrificed.

In the control animals (Group I), a tumor grew (>24 mm in diameter). Thirty days later, at which the experiment was finished, the difference between Group I and Group II was not statistically significant (P<0.0065, unpaired t-test). However, an average growth rate of Group I was larger than that of Group II. Furthermore, the important thing was that the difference between Group II and Group III was statistically significant (P<0.01) (FIG. 21).

INDUSTRIAL APPLICABILITY

According to the present invention, it is possible to provide a recombinant HSV having ability to kill specifically tumor cells such as human glioma in vivo and being safe and useful for treating a human glioma; and provide a therapeutic drug for a tumor such as a human glioma, containing the recombinant HSV as an active ingredient. When the recombinant HSV of the present invention is directly administered to a tumor tissue such as a human glioma, Musashi1 promoter specifically works only within a tumor such as human glioma cells. As a result, the recombinant HSV selectively proliferates within the tumor cells such as a human glioma, causing lysis of the tumor cells such as a glioma. In this manner, growth of the tumor tissue can be inhibited and destroyed. For example, KeM345, which is the recombinant HSV of the present invention, has intact ribonucleotide reductase gene and γ34.5 gene, which are inactivated in G207. Therefore, once KeM345 transmits to malignant glioma cells having Musashi1 expressed therein, γ34.5 is expressed by the Musashi1 promoter, although the safety to normal tissue is equivalent to that of G207. In this mechanism, viral replication corresponding to wild HSV can be induced, exerting a high cytotoxic effect (cytolytic ability) on the tumor cells. Furthermore, since a recombinant HSV KeM345 construct is equivalent to a virus, it can be easily obtained as a purified strain and proliferated in a stable state by being transmitted to culture cells. More specifically, if the virus of the GMP level is produced, clinical application thereof can be easily and quickly started. In addition, the high therapeutic effect of the virus can be greatly expected. A therapeutic drug selectively working on a malignant glioma and having extremely excellent cytolytic ability beyond expectation can be obtained, even compared with dvM345 (virus stock) of the present inventors.

The invention claimed is:

1. A recombinant herpes simplex virus (HSV) comprising: a transcription unit comprising a Musashi1 promoter operably linked to an HSV γ34.5 gene and HSV ribonucleotide reductase gene, and a poly A sequence terminating transcriptions of both genes wherein the transcription unit is inserted into an attenuated HSV viral DNA lacking a functional γ34.5 gene and lacking a functional ribonucleotide reductase gene.

2. The recombinant HSV according to claim 1, wherein the transcription unit is inserted into the ribonucleotide reductase gene site of the attenuated HSV.

3. A drug for expression in a Musashi1 expressing tumor cell, the composition comprising the recombinant HSV according to claim 1 or 2 and a carrier.

4. The drug according to claim 3, wherein the Musashi1 expressing tumor cell is a human glioma cell.

* * * * *